United States Patent
Wenefrida et al.

(10) Patent No.: US 9,888,637 B2
(45) Date of Patent: Feb. 13, 2018

(54) LSUAC HI PROTEIN RICE

(71) Applicant: Louisiana State University Agricultural Center, Payne, LA (US)

(72) Inventors: Ida Wenefrida, Payne, LA (US); Herry S. Utomo, Payne, LA (US); Steven Linscombe, Payne, LA (US)

(73) Assignee: Louisiana State University Agricultural Center, Baton Rouge, LA (US)

( * ) Notice: Subject to any disclaimer, the term of this patent is extended or adjusted under 35 U.S.C. 154(b) by 0 days.

(21) Appl. No.: 14/943,177

(22) Filed: Nov. 17, 2015

(65) Prior Publication Data

US 2017/0135304 A1     May 18, 2017

(51) Int. Cl.
*A01H 5/10* (2006.01)

(52) U.S. Cl.
CPC ..................... *A01H 5/10* (2013.01)

(58) Field of Classification Search
None
See application file for complete search history.

(56) References Cited

U.S. PATENT DOCUMENTS

| | | | |
|---|---|---|---|
| 6,956,154 B2 * | 10/2005 | Xie | A01H 5/10 435/410 |
| 7,141,725 B2 | 11/2006 | Linscombe | |
| 7,786,360 B2 | 8/2010 | Linscombe | |
| 8,589,080 B2 | 11/2013 | Morris et al. | |
| 8,841,525 B2 | 9/2014 | Linscombe | |
| 8,841,526 B2 | 9/2014 | Linscombe | |
| 8,946,528 B2 | 2/2015 | Linscombe | |
| 2004/0168232 A1 | 8/2004 | Groth et al. | |
| 2015/0096074 A1 | 4/2015 | Linscombe | |

* cited by examiner

*Primary Examiner* — Medina A Ibrahim
(74) *Attorney, Agent, or Firm* — McKee, Voorhees & Sease, PLC

(57) ABSTRACT

According to the invention, there is provided a novel rice cultivar, designated LSUAC Hi Protein Rice. 'LSUAC Hi Protein Rice' has up to an average 53% improvement in protein content with levels averaging 11%. The variety is described as semi-dwarf, and very early maturing. The invention relates to the seeds of rice cultivar LSUAC Hi Protein Rice, to the plants of rice cultivar LSUAC Hi Protein Rice, to plant parts of rice cultivar LSUAC Hi Protein Rice, to methods for producing a rice cultivar by crossing the rice cultivar LSUAC Hi Protein Rice with another rice cultivar, and to methods for producing a rice cultivar containing in its genetic material one or more backcross conversion traits or transgenes and to the backcross conversion rice plants and plant parts produced by those methods.

23 Claims, No Drawings

LSUAC HI PROTEIN RICE

FIELD OF THE INVENTION

The present invention relates to the field of plant breeding. In particular, this invention relates to a new rice variety designated "LSUAC Hi Protein Rice"

BACKGROUND OF THE INVENTION

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 cm to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium and short-grain cultivars cook moist and sticky. Long-grain cultivars have been traditionally grown in the southern states and generally receive higher market prices.

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics or grain quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of rice plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior crosses. The $F_1$ seed is produced by manual crosses between selected male-fertile parents or by using male sterility systems. These $F_1$s are selected for certain single gene traits such as semi-dwarf plant type, pubescence, awns, and apiculus color which indicate that the seed is truly a hybrid. Additional data on parental lines, as well as the phenotype of the $F_1$, influence the breeder's decision whether to continue with the specific cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an F1. An $F_2$ population is produced by selfing one or several $F_1$'s. Selection of the best individuals may begin in the F2 population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep, et. al, 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Rice, *Oryza sativa* L., is an important and valuable field crop. Thus, a continuing goal of plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

According to the invention, there is provided a novel rice cultivar designated LSUAC Hi Protein. This invention thus relates to the seeds of rice cultivar LSUAC Hi Protein, to the plants of rice LSUAC Hi Protein, and to methods for producing a rice plant produced by crossing rice LSUAC Hi Protein with itself or another rice plant.

Thus, any such methods using rice variety LSUAC Hi Protein are part of this invention: selfing, backcrosses, hybrid production, crosses to populations, and the like. All plants produced using rice variety LSUAC Hi Protein as a parent are within the scope of this invention. Advantageously, the rice variety could be used in crosses with other, different, rice plants to produce first generation ($F_1$) rice hybrid seeds and plants with superior characteristics.

In another aspect, the present invention provides for single gene converted plants of LSUAC Hi Protein. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant LSUAC Hi Protein. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, leaves, anthers, pistils, root tips, flowers, seeds, panicles, or stems. Still further, the present invention provides rice plants regenerated from the tissue cultures of the invention.

In another aspect, the present invention provides for producing a blend consisting of rice seed of inbred rice line LSUAC Hi Protein with rice seed of another rice inbred, rice variety or rice hybrid. The blend may also include a first quantity of seed of inbred rice line LSUAC Hi Protein with one, two, three, four, five or more quantities of rice seed of another rice hybrid, rice inbred or rice variety.

In another aspect, the present invention also provides for producing a blend of seed of inbred rice line LSUAC Hi Protein with seed of one, two, three, four, five or more of another rice hybrid, rice variety or rice inbred where inbred rice line LSUAC Hi Protein is present in proportions from 1% up to 95% of the blend. Another aspect of this invention is planting the blend produced with seeds of inbred rice line LSUAC Hi Protein and seeds of one, two three, four, five or more of another rice hybrid, rice variety or rice inbred and obtaining a crop with a mix of plants with inbred rice line LSUAC Hi Protein as a component. Further, another aspect of this invention is the harvest of seeds from a planted blend of plants of which inbred rice line LSUAC Hi Protein is a component of the blend for the purpose of utilizing such seeds for food, feed, as a raw material in industry or as a seed source for planting.

In addition to the exemplary aspects and embodiments described above, further aspects and embodiments will become apparent by study of the following description.

DEFINITIONS

In the description and tables which follow, a number of terms are used. In order to provide a clear and consistent understanding of the specification and claims, including the scope to be given such terms, the following definitions are provided:

1000 Grain Wt. The weight of 1000 rice grains as measured in grams.

Alkali Spreading Value. Indicator of gelatinization temperature and an index that measures the extent of disintegration of milled rice kernel in contact with dilute alkali solution. Standard long grains have 3 to 5 Alkali Spreading Value (intermediate gelatinization temperature).

Allele. The allele is any of one or more alternative forms of a genetic sequence. In a diploid cell or organism, the two alleles of a given genetic sequence occupy corresponding loci on a pair of homologous chromosomes.

Apparent Amylose Percent. The most important grain characteristic that describes cooking behavior in each grain class, or type, i.e., long-, medium- and short-grain. The percentage of the endosperm starch of milled rice that is amylose. Standard long grains contain 20% to 23% amylose. Rexmont type long grains contain 24% to 25% amylose. Short and medium grains contain 16% to 19% amylose. Waxy rice contains 0% amylose. Amylose values will vary over environments.

Backcrossing. Backcrossing is a process in which a breeder crosses progeny back to one of the parents one or more times, for example, a first generation hybrid $F_1$ with one of the parental genotype of the $F_1$ hybrid.

Breakdown. The peak viscosity minus the hot paste viscosity.

Cool Paste Viscosity. Viscosity measure of rice flour/water slurry after being heated to 95° C. and uniformly cooled to 50° C. (American Association of Cereal Chemist). Values less than 200 for cool paste indicate softer cooking types of rice.

Days to 50% heading. Average number of days from emergence to the day when 50% of all panicles are exerted at least partially through the leaf sheath. A measure of maturity.

Essentially all the physiological and morphological characteristics. A plant having essentially all the physiological and morphological characteristics of a specified plant refers to a plant having the same general physiological and morphological characteristics, except for those characteristics derived from a particular converted gene.

Final Viscosity. Viscosity at the end of the test or cold paste.

Grain Length (L). Length of a rice grain is measured as millimeters.

Grain Width (W). Width of a rice grain is measured as millimeters.

Grain Yield. Grain yield is measured in pounds per acre and at 12.0% moisture. Grain yield of rice is determined by the number of panicles per unit area, the number of fertile florets per panicle, and grain weight per floret.

Harvest Moisture. The percent of moisture of the grain when harvested.

Hot Paste Viscosity. Viscosity measure of rice flour/water slurry after being heated to 95° C. Lower values indicate softer and stickier cooking types of rice.

Length/Width (L/W) Ratio. This ratio is determined by dividing the average length (L) by the average width (W).

Lodging Resistance (also called Straw Strength). Lodging is measured as a subjective rating and is percentage of the plant stems leaning or fallen completely to the ground before harvest.

Peak Viscosity. The maximum viscosity attained during heating when a standardized instrument-specific protocol is applied to a defined rice flour-water slurry.

Plant Cell. As used herein, the term "plant cell" includes plant cells whether isolated, in tissue culture or incorporated in a plant or plant part.

Plant Height. Plant height in centimeters is taken from soil surface to the tip of the extended panicle at harvest.

Plant Part. As used herein, the term "plant part" includes leaves, stems, roots, seed, embryos, pollen, ovules, flowers, root tips, anthers, tissue, cells, axillary buds, and the like.

Plant Tissue Color Chart. Refers to the Munsell Color Chart for Plant Tissue which publishes an official botanical color chart quantitatively identifying colors according to a defined numbering system. The Munsell Color Chart for Plant Tissue may be purchased from Munsell Color Services, 617 Little Britain Road, Suite 102, New Windsor, N.Y. 12553-6148, USA, Part Number: 50150.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

RVA Viscosity. Rapid Visco Analyzer is a widely used laboratory instrument to examine paste viscosity, or thickening ability of milled rice during the cooking process.

Setback. Setback 1 is the final viscosity minus trough viscosity. Setback 2 is the final viscosity minus peak viscosity.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

Trough Viscosity. The minimum viscosity after the peak, normally occurring when the sample starts to cool.

DETAILED DESCRIPTION OF THE INVENTION

LSUAC Hi Protein Rice line was developed from cellular selections in a suspension cell culture system using a liquid culture medium containing elevated toxic levels of S-2-aminoethyl-L-cysteine (AEC). The suspension culture was established using calli that were induced from mature embryos of rice cv Cypress. Over 10 million cells were screened for AEC tolerance. Cells surviving from the treatment were rescued and plated onto semi solid regeneration media to produce plantlets. A total of 187 plantlets were regenerated from the cellular selection and transplanted in the greenhouse in 2006 to produce seed for field tests in the subsequent year. About 65% of the regenerated plants exhibited sterility from mild to severe. Plants with complete sterility were discarded. A total of 132 recovered plants (designated as $M_1$s composed of 65 fertile and 67 partially sterile lines) were planted in headrows in a field at the Rice Research Station. Protein content of each line was determined based on samples collected from three separate panicles and three bulked samples of row harvest. In every test and selection, Cypress and Cocodrie were imbedded in the test as cultivar checks. The $M_1$ line designated as 06CY-58120018 planted in row number 1057 was selected for advancement based on its protein content and fertility. Ten panicles from the 06CY-58120018 row were harvested and used in headrow planting in 2008. Twenty full and disease-free panicles were selected from each row of the line. Protein content analyses were conducted in each panicle collected. Rice grains within panicles of this line that consistently showed high protein content and fertility were bulked and advanced. The bulk seed was used the next year and planted in 48 rows and two rows of checks. A total of 200 panicles were collected and subjected to protein analyses for selection and purification. The seed from selected panicles were bulked. A similar test on the line was conducted the following year for further selection and purification. The seed from selected panicles was bulked and then used in replicated trials. The purified 06-CPHP057 entered preliminary yield (PY) trials and multi-location trials. Finally seed increase was done in the Puerto Rico winter nursery.

LSUAC Hi Protein Rice is a semidwarf line that was derived from the rice cultivar Cypress well known for its excellent milling quality. It is a very early maturing line and displayed good yield potential, grain quality characteristics, and lodging resistance in yield testing for several years. Yield, milling, agronomic, grain dimension, and cereal chemistry data is herein.

In each generation following mutation and cellular selection ($M_1$ to $M_6$), the line was selected for consistent high grain protein content and uniformity and purity of its agronomic traits.

Area of Adaptation—LSUAC Hi Protein Rice is adapted to the rice growing areas in Louisiana. It has shown its good adaptation in Puerto Rico as well.

The line averages 91.5 cm in height, which is similar to Cypress. LSUAC Hi Protein Rice averages 85 days from emergence to 50% heading, which is similar to Cypress and 3 days later than Cocodrie. The leaves of this experimental line are dark green in color and display an erect leaf angle. It has a purple apiculus. Its lemma and palea are gold at maturity and gold furrows and straw background, glabrous and typically non-awned. The brand is light brown and non-glutinous with average 21.8% of amylose content. The grain has intermediate gelatinization temperature.

This high protein line has been observed for five generations of selections, purifications, and enhancement and has exhibited very high uniformity and stability in both protein content and most of agronomic characteristics.

A variety description of LSUAC Hi Protein Rice is provided in Table 1.

TABLE 1

| Variety Description Information | |
|---|---|
| TRAIT | |
| MATURITY | |
| Number of days | 85 |
| 0 days same as | Cypress |
| 3 days later than | Cocodrie |
| Maturity Class | 1 = very early (85 days or less) |
| CULM | |
| Angle (Degrees from Perpendicular after Flowering) | 1 = erect (less than 30°) |

TABLE 1-continued

Variety Description Information

| TRAIT | |
|---|---|
| Length | 91.5 cm |
| Same as | Cypress |
| 1.6 cm longer than | Cocodrie |
| Height class | 1 = short (≤95 cm) |
| Internode color (after flowering) | Green |
| Strength (Lodging resistance) | Moderately strong (most plants leaning) |
| FLAG LEAF | |
| Length | 31.3 cm |
| Pubsescence | glabrous |
| Leaf Angle | intermediate |
| Blade Color | green |
| Basal Leaf Sheath | green |
| 1. LIGULE | 2. |
| length | 4.1 mm (from base of collar to tip at late vegetative stage) |
| Color (late vegetative stage) | Purple lines |
| shape | Acute to acuminate |
| Collar color (late vegetative stage) | Pale green |
| Auricle color | purple |
| PANICLE | |
| length | 20.3 mm |
| type | intermediate |
| Secondary branching | light |
| Exertion (near maturity) | 90-99% |
| Shattering (at maturity) | Low ≤5% |
| Threshability | easy |
| GRAIN (Spiklet) | |
| Awns (after full heading) | Short and partly awned |
| Apiculus color (at maturity) | purple |
| Apiculus color (after full heading) | purple |
| Stigma color | Light green |
| Lemma and palea color (at maturity) | Gold and/or gold furrows on straw background |
| Lemma and palea pubescence | glabrous |
| Spiklet sterility (at maturity) | Highly fertile (>90%) |
| GRAIN (Seed) | |
| Seed coat (Bran) color | Speckeled Brown |
| Endosperm type | nonglutinous (nonwaxy) |
| Endosperm tanslucency | clear |
| Endosperm chalkiness | Small (less than 10% of sample) |
| Scent | nonscented |
| Paddy | Long (3.4:1 and more) |
| Brown | Long (3.4:1 and more) |
| Milled | Long (3.4:1 and more) |
| Paddy (measurements from grain) | Length (mm) 9.34 |
| | Width (mm) 2.43 |
| | Thickness (mm) 1.96 |
| | L/W ratio 3.84 |
| | 1000 grains (grams) 24.87 |
| Brown (measurements from grain) | Length (mm) 7.09 |
| | Width (mm) 2.20 |
| | Thickness (mm) 1.78 |
| | L/W ratio 3.59 |
| | 1000 grains (grams) 21.00 |
| Milled (measurements from grain) | Length (mm) 6.97 |
| | Width (mm) 2.11 |
| | Thickness (mm) 1.74 |
| | L/W ratio 3.30 |
| | 1000 grains (grams) 19.10 |
| Milling yield (% white kernel (head) Rice to Rough Rice) | 60.5 |
| Milling % protein | 11 |
| Milling % amylose | 21.8 |
| Alkali spreading value | 5 (1.7% KOH Solution) |
| Gelatination temperature type | Intermediate |
| RESISTANCE TO LOW TEMPERATURE | |
| Germination and seedling vigor | medium |
| Flowering (spikelet fertility) | medium |
| SEEDLING VIGOR NOT RELATED TO LOW TEMPERATURE | medium |
| BLAST RESISTANCE (*PYCULARIA ORYZAE*) | |
| Group 1B Number 1 | Moderately resistant |
| Group 1B Number 49 | Moderately resistant |
| Group 1C Number 17 | Moderately resistant |
| Group IG Number 1 | resistant |
| Group IH Number 1 | Resistant |
| RESISTANCE TO OTHER DISEASES | |
| Narrow Brown Leaf Spot | intermediate |
| Straight Head | Moderately Resistant |
| Sheath Blight (*Rhizoctonia solani*) | Moderately Susceptible |
| INSECT RESISTANCE | |
| Rice Stink Bug (*Oegalus pugnax*) | susceptible |
| Rice Water Weevil (*Lissorhoptrus oryzopholis*) | susceptible |

LSUAC Hi Protein Rice has an average protein content of 11%, about 53% improvement from the protein content of the original line (Cypress) from which it was derived (mutated).

LSUAC Hi Protein Rice closely resembles the rice variety Cypress and, therefore, differs with other rice cultivars. Its main distinctness to Cypress and other rice cultivars is its high grain protein content. Despite its close similarity with the cultivar Cypress in amylose content, its grain has distinct cooking characteristics due to its increased protein content.

TABLE 2

Summary of yield, milling, agronomic and physiochemical properties of long-grain LSUAC Hi Protein Rice, Cypress, and Cocodrie.

| | Performance | | | | |
|---|---|---|---|---|---|
| Trait | LSUAC Hi Protein Rice | CYPRESS | COCODRIE | Number of Tests | Reference |
| Yield Total | 6746.5 | 7484.7 | 7640.7 | 11 | Tables 2 to 12 |
| Protein Content Amylose % | 11.05 | 7.23 | 7.16 | 8 | Tables 2 to 10 |
| Gel Type | Intermediate high | Intermediate high | Intermediate high | | Table 13 |

TABLE 2-continued

Summary of yield, milling, agronomic and physiochemical properties of long-grain LSUAC Hi Protein Rice, Cypress, and Cocodrie.

| Trait | Performance LSUAC Hi Protein Rice | CYPRESS | COCODRIE | Number of Tests | Reference |
|---|---|---|---|---|---|
| Cook Type | Intermediate | Ex. High amylose | Ex. High amylose | | Table 13 |
| Length-Rough | 9.34 | 9.31 | 9.25 | | Table 14 |
| Width-Rough | 2.43 | 2.50 | 2.43 | | Table 14 |
| L/W Ratio-Rough | 3.84 | 3.74 | 3.81 | | Table 14 |
| Thickness-Rough | 1.96 | 1.96 | 1.91 | | Table 14 |
| Length-Brown | 7.09 | 7.14 | 7.06 | | Table 14 |
| Width-Brown | 2.20 | 2.21 | 2.14 | | Table 14 |
| L/W Ratio-Brown | 3.59 | 3.23 | 3.30 | | Table 14 |
| Thickness-Brown | 1.78 | 1.78 | 1.67 | | Table 14 |
| Length-Milled | 6.97 | 6.99 | 6.87 | | Table 14 |
| Width-Milled | 2.11 | 2.11 | 2.05 | | Table 14 |
| L/W Ratio-Milled | 3.30 | 3.31 | 3.35 | | Table 14 |
| Thickness-Milled | 1.74 | 1.75 | 1.67 | | Table 14 |
| Vigor | 4.7 | 4.3 | 4.7 | 11 | Tables 2 to 12 |
| Height | 91.5 | 91.5 | 89.9 | 11 | Tables 2 to 12 |
| Days to 50% | 85.2 | 85.2 | 82.4 | 11 | Tables 2 to 12 |
| Sheath Blight* | 7 | 7 | 9 | | |
| Leaf Blast* | — | — | — | | |
| Rotten Neck Blast* | — | — | — | | |
| Panicle Blight* | — | — | — | | |
| Narrow Brown Leaf Spot* | 5 | 5 | 1 | | |
| Leaf Smut* | — | — | 7 | | |
| Brown Spot* | — | — | — | | |
| Straighthead* | 3 | 3 | 7 | | |

*0-9 scale where higher numbers indicate greater susceptibility.

TABLE 3

PY - RRS

| | VIG | HTE | HDT | YIELD | WHOLE | TOTAL | PROT |
|---|---|---|---|---|---|---|---|
| LSUAC Hi Protein Rice | 4.5 | 90.4 | 85.3 | 6944.0 | 62.1 | 69.2 | 11.3 |
| CYPRESS | 4.5 | 89.3 | 85.0 | 7204.5 | 63.4 | 70.1 | 7.4 |
| COCODRIE | 3.5 | 85.6 | 82.3 | 7613.2 | 62.6 | 69.8 | 7.1 |

TABLE 4

PY - RRS

| | VIG | HTE | HDT | YIELD | WHOLE | TOTAL | PROT |
|---|---|---|---|---|---|---|---|
| LSUAC Hi Protein Rice | 4.5 | 92.4 | 85.6 | 7051.0 | 60.0 | 68.1 | 10.9 |
| CYPRESS | 4.0 | 93.2 | 87.3 | 7432.8 | 62.3 | 69.4 | 7.1 |
| COCODRIE | 4.5 | 96.1 | 83.0 | 7513.4 | 60.1 | 68.2 | 7.3 |

TABLE 5

CA - RRS

| | VIG | HTE | HDT | YIELD | WHOLE | TOTAL | PROT |
|---|---|---|---|---|---|---|---|
| LSUAC Hi Protein Rice | 5.0 | 91.4 | 84.3 | 6760.6 | 64.2 | 69.2 | 10.8 |
| CYPRESS | 4.0 | 92.6 | 85.0 | 7427.9 | 63.1 | 69.1 | 7.0 |
| COCODRIE | 4.5 | 94.8 | 81.0 | 7673.8 | 62.4 | 68.3 | 6.8 |

TABLE 6

CA - JEFF DAVIS

| | VIG | HTE | HDT | YIELD | WHOLE | TOTAL | PROT |
|---|---|---|---|---|---|---|---|
| LSUAC Hi Protein Rice | 5.0 | 81.3 | 87.3 | 5643.9 | 63.7 | 70.1 | 11.5 |
| CYPRESS | 3.7 | 82.3 | 86.0 | 6235.4 | 64.9 | 70.5 | 7.6 |
| COCODRIE | 4.7 | 76.3 | 84.0 | 6525.9 | 63.8 | 69.8 | 7.1 |

TABLE 7

CA - VERMILION

| | VIG | HTE | HDT | YIELD | WHOLE | TOTAL | PROT |
|---|---|---|---|---|---|---|---|
| LSUAC Hi Protein Rice | 4.3 | 86.7 | 85.0 | 6138.7 | 61.9 | 68.9 | 10.7 |
| CYPRESS | 4.0 | 88.7 | 84.6 | 6665.6 | 60.8 | 69.1 | 6.8 |
| COCODRIE | 3.3 | 88.0 | 82.6 | 7267.8 | 60.4 | 69.7 | 7.1 |

TABLE 8

CA - EVANGELINE

| | VIG | HTE | HDT | YIELD | WHOLE | TOTAL | PROT |
|---|---|---|---|---|---|---|---|
| LSUAC Hi Protein Rice | 4.3 | 88.3 | 83.3 | 5881.8 | | | 11.1 |
| CYPRESS | 4.0 | 89.0 | 83.0 | 6963.5 | | | 7.4 |
| COCODRIE | 4.0 | 84.7 | 81.3 | 7215.7 | | | 7.6 |

TABLE 9

CA - RRS

| | VIG | HTE | HDT | YIELD | WHOLE | TOTAL | PROT |
|---|---|---|---|---|---|---|---|
| LSUAC Hi Protein Rice | 4.0 | 89.2 | 85.3 | 6341.5 | 45.2 | 62.1 | 10.8 |
| CYPRESS | 4.5 | 91.4 | 86.0 | 6821.1 | 51.5 | 64.1 | 7.0 |
| COCODRIE | 4.0 | 81.3 | 83.3 | 7004.2 | 42.4 | 63.2 | 7.3 |

TABLE 10

CA - JEFF DAVIS

| | VIG | HTE | HDT | YIELD | WHOLE | TOTAL | PROT |
|---|---|---|---|---|---|---|---|
| LSUAC Hi Protein Rice | 4.0 | 90 | 87.0 | 8151.0 | | | |
| CYPRESS | 4.0 | 90 | 86.3 | 8595.0 | | | |
| COCODRIE | 4.0 | 89 | 84.0 | 8857.0 | | | |

TABLE 11

CA - RICE RESEARCH STATION

| | VIG | HTE | HDT | YIELD | WHOLE | TOTAL | PROT |
|---|---|---|---|---|---|---|---|
| LSUAC Hi Protein Rice | 5.3 | 99.3 | 84.3 | 8030.4 | 66.7 | 74.9 | 11.3 |
| CYPRESS | 5.3 | 100.7 | 85.0 | 8931.6 | 67.8 | 75.4 | 7.5 |
| COCODRIE | 5.0 | 102.0 | 82.3 | 8690.6 | 65.4 | 74.1 | 7.0 |

TABLE 12

CA - EVANGELINE, LA

| | VIG | HTE | HDT | YIELD | WHOLE | TOTAL | PROT |
|---|---|---|---|---|---|---|---|
| LSUAC Hi Protein Rice | 5.3 | 99.8 | 84.6 | 7519.5 | | | |
| CYPRESS | 4.0 | 94.3 | 84.0 | 8058.4 | | | |
| COCODRIE | 9.0 | 95.5 | 80.6 | 8505.8 | | | |

TABLE 13

CA - VERMILLION, LA

| | VIG | HTE | HDT | YIELD | WHOLE | TOTAL | PROT |
|---|---|---|---|---|---|---|---|
| LSUAC Hi Protein Rice | 6.0 | 98.3 | 86.0 | 5770.9 | | | |
| CYPRESS | 5.7 | 95.7 | 85.3 | 7996.2 | | | |
| COCODRIE | 5.7 | 96.3 | 83.0 | 7179.8 | | | |

TABLE 14

Cereal Chemistry of LSUAC Hi Protein Rice and Selected Check Cultivars

| | APPARENT AMYLOSE CONTENT (%) | | | |
|---|---|---|---|---|
| | Average | Min. | Max | COOK TYPE |
| LSUAC Hi Protein Rice | 21.8 | | | Intermediate |
| CYPRESS | 20.9 | | | Extra High Amylose |
| COCODRIE | 23.2 | | | Extra High Amylose |

TABLE 15

Grain dimensions of LSUAC Hi Protein Rice, Cypress, and Cocodrie.

| Genotype | Type | Length | Width | Thickness | L/W | Wgt (mg) |
|---|---|---|---|---|---|---|
| LSUAC Hi Protein Rice | Rough | 9.34 | 2.43 | 1.96 | 3.84 | 24.87 |
| CYPRESS | Rough | 9.31 | 2.5 | 1.96 | 3.72 | 24.99 |
| COCODRIE | Rough | 9.25 | 2.43 | 1.91 | 3.81 | 25.41 |
| LSUAC Hi Protein Rice | Brown | 7.09 | 2.20 | 1.78 | 3.59 | 21.00 |
| CYPRESS | Brown | 7.14 | 2.21 | 1.78 | 3.23 | 21.00 |
| COCODRIE | Brown | 7.06 | 2.14 | 1.67 | 3.30 | 21.13 |
| LSUAC Hi Protein Rice | Milled | 6.97 | 2.11 | 1.74 | 3.30 | 19.10 |
| CYPRESS | Milled | 6.99 | 2.11 | 1.75 | 3.31 | 19.12 |
| COCODRIE | Milled | 6.87 | 2.05 | 1.67 | 3.35 | 19.42 |

Statistical Analysis

Measurable characteristics were assessed in several localities or dates and the results were analyzed separately. Unless otherwise indicated, the statistical analyses were performed using T-test. The results presented in actual t-value and probability values p[t] and are statically different at the 95% confidence level. The standard of deviation for each variety in the comparisons is presented.

Other Embodiments

This invention is also directed to methods for producing a rice plant by crossing a first parent rice plant with a second parent rice plant, wherein the first parent rice plant or second parent rice plant is the rice plant from cultivar LSUAC Hi Protein Rice. Further, both the first parent rice plant and second parent rice plant may be from cultivar LSUAC Hi Protein Rice. Therefore, any methods using rice cultivar LSUAC Hi Protein Rice are part of this invention, such as selfing, backcrosses, hybrid breeding, and crosses to populations. Plants produced using rice cultivar LSUAC Hi Protein Rice as at least one parent is within the scope of this invention.

In one aspect of the invention, methods for developing novel plant types are presented. In one embodiment the specific type of breeding method is pedigree selection, where both single plant selection and mass selection practices are employed. Pedigree selection, also known as the "Vilmorin system of selection," is described in Fehr, Walter; Principles of Cultivar Development, Volume I, Macmillan Publishing Co., which is hereby incorporated by reference.

In rice breeding, lines may be selected for certain desired appropriate characteristics. To optimize crossing, it is important to note that rice is an obligate self-pollinating species. This means that the pollen is shed before stigma emergence, assuring 100% self-fertilization. Since each rice flower is an aggregate of about 10-20 individual florets (typical of the Compositae family), removal of the anther tubes containing the pollen is performed by procedures well known in the art of rice breeding.

In one embodiment, the pedigree method of breeding is practiced where selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny row the preceding generation.

In addition to crossing, selection may be used to identify and isolate new rice lines. In rice selection, rice seeds are planted, the plants are grown and single plant selections are made of plants with desired characteristics. Seed from the single plant selections may be harvested, separated from seeds of the other plants in the field and re-planted. The plants from the selected seed may be monitored to determine if they exhibit the desired characteristics of the originally selected line. Selection work is preferably continued over multiple generations to increase the uniformity of the new line.

In a preferred embodiment, the development of commercial rice cultivars requires the development of rice varieties, the crossing of these varieties, and the evaluation of the crosses. Pedigree breeding and recurrent selection breeding methods may be used to develop cultivars from breeding populations. Breeding programs may combine desirable traits from two or more varieties or various broad-based sources into breeding pools from which cultivars are developed by selfing and selection of desired phenotypes. The new cultivars may be crossed with other varieties and the hybrids from these crosses are evaluated to determine which have commercial potential.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into rice varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Rice is an important and valuable vegetable crop. Thus, a continuing goal of rice plant breeders is to develop stable, high yielding rice cultivars that are agronomically sound. To accomplish this goal, the rice breeder preferably selects and develops rice plants with traits that result in superior cultivars.

This invention also is directed to methods for producing a rice cultivar plant by crossing a first parent rice plant with a second parent rice plant wherein either the first or second parent rice plant is a rice plant of the line LSUAC Hi Protein Rice. Further, both first and second parent rice plants can come from the cultivar LSUAC Hi Protein Rice. Still further, this invention also is directed to methods for producing a cultivar LSUAC Hi Protein Rice-derived rice plant by crossing cultivar LSUAC Hi Protein Rice with a second rice plant and growing the progeny seed, and repeating the crossing and growing steps with the cultivar LSUAC Hi Protein Rice-derived plant from 0 to 7 times. Thus, any such methods using the cultivar LSUAC Hi Protein Rice are part of this invention: selfing, backcrosses, hybrid production, crosses to populations, and the like. All plants produced using cultivar LSUAC Hi Protein Rice as a parent is within the scope of this invention, including plants derived from cultivar LSUAC Hi Protein Rice. Advantageously, the cultivar is used in crosses with other, different, cultivars to produce first generation ($F_1$) rice seeds and plants with superior characteristics.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, seeds, roots, anthers, and the like.

As is well known in the art, tissue culture of rice can be used for the in vitro regeneration of a rice plant. Tissue culture of various tissues of rices and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce rice plants having the physiological and morphological characteristics of variety LSUAC Hi Protein Rice.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as transgenes. Over the last fifteen to twenty years several methods for producing transgenic plants have been developed, and the present invention, in particular embodiments, also relates to transformed versions of the claimed line.

Plant transformation preferably involves the construction of an expression vector that will function in plant cells. Such a vector may comprise DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Rice Transformation

Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990<Hille et al., Plant Mol. Biol. 7:171 (1986). Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include .beta.-glucuronidase (GUS), .beta.-galactosidase, luciferase and chloramphenicol, acetyltransferase. Jefferson, R. A., Plant Mol. Biol. Rep. 5:387 (1987), Teeri et al., EMBO J. 8:343

(1989), Koncz et al., Proc. Natl. Acad. Sci U.S.A. 84:131 (1987), DeBlock et al., EMBO J. 3:1681 (1984).

Recently, in vivo methods for visualizing GUS activity that do not require destruction of plant tissue have been made available. Molecular Probes publication 2908, Imagene Green™, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters

Genes included in expression vectors preferably are driven by nucleotide sequence comprising a regulatory element, for example, a promoter. Several types of promoters are now well known in the transformation arts, as are other regulatory elements that can be used alone or in combination with promoters.

As used herein, promoter includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive promoter" is a promoter which is active under most environmental conditions.

A. Inducible Promoters

An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent. Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter may be operably linked to a gene for expression in rice or the constitutive promoter may operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., Nature 313:810-812 (1985) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT application WO96/30530.

C. Tissue-Specific or Tissue Preferred Promoters

A tissue-specific promoter may be operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., Structure and Organization of Two Divergent Alpha-Amylase Genes from Barley, Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is rice. In another preferred embodiment, the biomass of interest is seed. For transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons may involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. Tomato encodes a protein kinase); Mindrinos et al., Cell 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotoch. Biochem. 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung rice calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1, 4-D-galacturonase. See Lamb at al., Bio/Technology 10:1436 (1992). The cloning and characterization of a gene which encodes a rice endopolygalacturonase-inhibiting protein is described by Toubart et al., Plant J. 2:367 (1992).

R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

S. A rice mosaic potyvirus (LMV) coat protein gene introduced into *Lactuca sativa* in order to increase its resistance to LMV infection. See Dinant et al., Molecular Breeding. 1997, 3: 1, 75-86.

2. Genes that Confer Resistance to an Herbicide, for Example:

A. A herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase PAT bar genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in Transgenic Research. 1999, 8: 1, 33-44 that discloses *Lactuca sativa* resistant to glufosinate. European patent application No. 0 333 033 to Kumada at al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., Theor. Appl. Genet. 83:435 (1992).

C. A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282, 837; 5,767,373; and international publication WO 01/12825.

3. Genes that Confer or Contribute to a Value-Added Trait, Such as:

A. Increased iron content of the rice, for example by transforming a plant with a soybean ferritin gene as described in Goto et al., Acta Horticulturae. 2000, 521, 101-109. Parallel to the improved iron content enhanced growth of transgenic rices was also observed in early development stages.

B. Decreased nitrate content of leaves, for example by transforming a rice with a gene coding for a nitrate reductase. See for example Curtis et al., Plant Cell Report. 1999, 18: 11, 889-896.

C. Increased sweetness of the rice by transferring a gene coding for monellin that elicits a flavor sweeter than sugar on a molar basis. See Penarrubia et al., Biotechnology. 1992, 10: 5, 561-564.

D. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

E. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* .alpha.-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Rice Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., Science 227:1229 (1985). Curtis et al., Journal of Experimental Botany. 1994, 45: 279, 1441-1449, Torres et al., Plant cell Tissue and Organic Culture. 1993, 34: 3, 279-285, Dinant et al., Molecular Breeding. 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao, F. J. L., et al. Pl. Cell. Rep. 12(9, July), 483-490 (1993). Aragao, Theor. Appl. Genet. 93: 142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992).

Another method for physical delivery of DNA to plants is sonication of target cells. Zhang et al., Bio/Technology 9:996 (1991). Alternatively, liposome or spheroplast fusion has been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-omithine has also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994). See also Chupean et al., Biotechnology. 1989, 7: 5, 503-508.

Following transformation of rice target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic rice line. Alternatively, a genetic trait that has been engineered into a particular rice cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term rice plant, cultivar or rice line is used in the context of the present invention, this also includes any gene conversions of that line. The term gene converted plant as used herein refers to those rice plants which are developed by a plant breeding technique called backcrossing wherein essentially all of the desired morphological and physiological characteristics of a cultivar are recovered in addition to the gene transferred into the line via the backcrossing technique. Backcrossing methods can be used with the present invention to improve or introduce a characteristic into the line. The term backcrossing as used herein refers to the repeated crossing of a hybrid progeny back to one of the parental rice plants for that line. The parental rice plant that contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent cultivar are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. Gene traits may or may not be transgenic, examples of these traits include but are not limited to, herbicide resistance, resistance for bacterial, fungal, or viral disease, insect resistance, enhanced nutritional quality, industrial usage, yield stability, yield enhancement, male sterility, modified fatty acid metabolism, and modified carbohydrate metabolism. These genes are generally inherited through the nucleus. Several of these gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of rice and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce rice plants having the physiological and morphological characteristics of cultivar LSUAC Hi Protein Rice.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a rice plant by crossing a first parent rice plant with a second parent rice plant wherein the first or second parent rice plant is a rice plant of cultivar LSUAC Hi Protein Rice. Further, both first and second parent rice plants can come from rice cultivar LSUAC Hi Protein Rice. Thus, any such methods using rice cultivar LSUAC Hi Protein Rice are part of this invention: selfing, backcrosses, hybrid production, crosses to populations, and the like. All plants produced using rice cultivar LSUAC Hi Protein Rice as at least one parent are within the scope of this invention, including those developed from cultivars derived from rice cultivar LSUAC Hi Protein Rice. Advantageously, this rice cultivar could be used in crosses with other, different, rice plants to produce the first generation ($F_1$) rice hybrid seeds and plants with superior characteristics. The cultivar of the invention can also be used for transformation where exogenous genes are introduced and expressed by the cultivar of the invention. Genetic variants created either through traditional breeding methods using rice cultivar LSUAC Hi Protein Rice or through transformation of cultivar LSUAC Hi Protein Rice by any of a number of protocols known to those of skill in the art are intended to be within the scope of this invention.

The following describes breeding methods that may be used with rice cultivar LSUAC Hi Protein Rice in the development of further rice plants. One such embodiment is a method for developing cultivar LSUAC Hi Protein Rice progeny rice plants in a rice plant breeding program comprising: obtaining the rice plant, or a part thereof, of cultivar LSUAC Hi Protein Rice, utilizing said plant or plant part as a source of breeding material, and selecting a rice cultivar LSUAC Hi Protein Rice progeny plant with molecular markers in common with cultivar LSUAC Hi Protein Rice and/or with morphological and/or physiological characteristics selected from the characteristics listed in Table 1. Breeding steps that may be used in the rice plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method which may be used involves producing a population of rice cultivar LSUAC Hi Protein Rice-progeny rice plants, comprising crossing cultivar LSUAC Hi Protein Rice with another rice plant, thereby producing a population of rice plants, which, on average, derive 50% of their alleles from rice cultivar LSUAC Hi Protein Rice. A plant of this population may be selected and repeatedly selfed or sibbed with a rice cultivar resulting from these successive filial generations. One embodiment of this invention is the rice cultivar produced by this method and that has obtained at least 50% of its alleles from rice cultivar LSUAC Hi Protein Rice.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes rice cultivar LSUAC Hi Protein Rice progeny rice plants comprising a combination of at least two cultivar LSUAC Hi Protein Rice traits selected from the group consisting of those listed in Table 1 or the cultivar LSUAC Hi Protein Rice combination of traits listed above, so that said progeny rice plant is not significantly different for said traits than rice cultivar LSUAC Hi Protein Rice as determined at the 5% significance level when grown in the same environmental conditions. Using techniques described herein, molecular markers may be used to identify said progeny plant as a rice cultivar LSUAC Hi Protein Rice progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of rice cultivar LSUAC Hi Protein Rice may also be characterized through their filial relationship with rice cultivar LSUAC Hi Protein Rice, as for example, being within a certain number of breeding crosses of rice cultivar LSUAC Hi Protein Rice. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice cultivar LSUAC Hi Protein Rice and its progeny. For example, progeny produced by the methods described herein may be within 1, 2, 3, 4 or 5 breeding crosses of rice cultivar LSUAC Hi Protein Rice.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

Deposits

Applicant(s) have made a deposit of at least 2500 seeds of Rice Cultivar LSUAC Hi Protein Rice with the American Type Culture Collection (ATCC), Manassas, Va. 20110 USA, ATCC Deposit No. PTA-124621. The seeds deposited with the ATCC on Nov. 22, 2017 were taken from the deposit maintained by The LSU AgCenter Rice Research Station 1373 Caffey Road, Rayne, La. 70578, since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, a deposit of at least 2500 seeds of cultivar LSUAC Hi Protein Rice with the American type Culture Collection (ATCC), 10801 University Boulevard, Manassas, Va. 20110-2209. This deposit of the rice cultivar LSUAC Hi Protein Rice will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have satisfied all the requirements of 37 C.F.R. §§ 1.801-1.809, including providing an indication of the viability of the sample. Applicants have no authority to waive any restrictions imposed by law on the transfer of biological material or its transportation in commerce. Applicants do not waive any infringement of their rights granted under this patent or under the Plant Variety Protection Act (7 USC 2321 et seq.).

What is claimed is:

1. A seed of rice cultivar designated LSUAC Hi Protein Rice, wherein a representative sample of seed of said cultivar was deposited under ATCC Accession No. PTA-124621.

2. A rice plant, or a part thereof, produced by growing the seed of claim 1.

3. The rice plant or part thereof, of claim 2 having approximately 11% seed protein content.

4. A tissue culture of cells produced from the plant of claim 2, wherein said cells of the tissue culture are produced from a plant part selected from the group consisting of embryo, meristematic cell, leaf, cotyledon, hypocotyl, stem, root, root tip, pistil, anther, flower, seed and pollen.

5. A protoplast produced from the plant of claim 2.

6. A protoplast produced from the tissue culture of claim 3.

7. A method for producing a progeny rice plant, wherein the method comprises crossing the plant of claim 2 with a different rice plant and harvesting the resultant progeny rice seed.

8. A progeny rice seed produced by the method of claim 7 having an average protein content of 11% of greater.

9. A progeny rice plant, or a part thereof, produced by growing said seed of claim 8.

10. A method of producing a male sterile rice plant wherein the method comprises transforming the rice plant of claim 2 with a nucleic acid molecule that confers male sterility.

11. A male sterile rice plant produced by the method of claim 10.

12. A method for producing an herbicide resistant rice plant wherein the method comprises transforming the rice plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

13. An herbicide resistant rice plant produced by the method of claim 12.

14. A method of producing an insect resistant rice plant wherein the method comprises transforming the rice plant of claim 2 with a transgene that confers insect resistance.

15. An insect resistant rice plant produced by the method of claim 14.

16. The rice plant of claim 15 wherein the transgene encodes a *Bacillus thuringiensis* endotoxin.

17. A method of producing a disease resistant rice plant wherein the method comprises transforming the rice plant of claim 2 with a transgene that confers disease resistance.

18. A disease resistant rice plant produced by the method of claim 17.

19. A method of producing a rice plant with a value-added trait, wherein the method comprises transforming the rice plant of claim 2 with a transgene encoding one or more of a fructosyltransferase, levansucrase, alpha-amylase, invertase and starch branching enzyme or encoding an antisense of stearyl-ACP desaturase.

20. A rice plant with a value-added trait produced by the method of claim 19.

21. A method of introducing a desired trait from rice cultivar LSUAC Hi Protein Rice into a second rice cultivar wherein the method comprises:
- a) crossing a LSUAC Hi Protein Rice plant grown from LSUAC Hi Protein Rice seed, wherein a representative sample of seed was deposited under ATCC Accession No. PTA-124621, with a plant of second rice cultivar to produce $F_1$ progeny plants, wherein the desired trait is protein content;
- b) selecting one or more progeny plants that have the desired trait to produce selected progeny plants;
- c) crossing the selected progeny plants with the second rice cultivar plants to produce backcross progeny plants;
- d) selecting for backcross progeny plants that have the desired trait; and
- e) repeating steps (c) and (d) three or more times in succession to produce selected fourth or higher backcross progeny plants that comprise the desired trait and essentially all of the physiological and morphological characteristics of said second rice cultivar.

22. A method of producing a blend of rice seed wherein the method comprises: a. providing a first quantity of rice seed of claim 1; b. providing a second quantity of rice seed of another rice variety, and c. producing a blend comprised of mixing said first quantity of rice seed with said second quantity of rice seed.

23. The method of claim 22, wherein said blend consists of seeds from a third, fourth or fifth rice variety.

\* \* \* \* \*